United States Patent
Bornzin et al.

(10) Patent No.: US 7,194,304 B1
(45) Date of Patent: Mar. 20, 2007

(54) IMPLANTABLE CARDIAC DEFIBRILLATION ASSEMBLY INCLUDING A SELF-EVALUATION SYSTEM AND METHOD

(75) Inventors: Gene A. Bornzin, Simi Valley, CA (US); Eric Falkenberg, Simi Valley, CA (US); Mark W. Kroll, Simi Valley, CA (US); Gabriel A. Mouchawar, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 365 days.

(21) Appl. No.: 10/702,562

(22) Filed: Nov. 5, 2003

(51) Int. Cl.
*A61N 1/365* (2006.01)
(52) U.S. Cl. ......................................................... 607/7
(58) Field of Classification Search ................. 607/4–8
See application file for complete search history.

(56) References Cited

U.S. PATENT DOCUMENTS

| | | | |
|---|---|---|---|
| 5,237,991 A | 8/1993 | Baker, Jr. et al. | 607/27 |
| 5,564,422 A | 10/1996 | Chen et al. | 128/697 |
| 6,216,036 B1 | 4/2001 | Jenkins et al. | 607/27 |
| 6,292,697 B1 | 9/2001 | Roberts | 607/27 |
| 6,345,200 B1 | 2/2002 | Mouchawar et al. | 607/8 |
| 6,859,664 B2 | 2/2005 | Daum et al. | 607/5 |

OTHER PUBLICATIONS

Wharton, J.M, MD et al., "*Cardiac Potential and Potential Fields Generated by Single, Combined, and Sequential Shocks During Ventricular Defibrillation*," CIRCULATION (1992); pp. 1510-1523.
Zipes, Douglas P., MD, FACC et al., "*Termination of Ventricular Fibrillation In Dogs By Depolarizing a Critical Amount of Myocardium*," Amer. J. Cardiology (Jul. 1975); vol. 36:pp. 37-44.

*Primary Examiner*—Scott M. Getzow

(57) ABSTRACT

An implantable cardiac defibrillation assembly includes at least one implantable lead having a defibrillation electrode adapted for placement in a chamber of the heart. The lead includes a connector. The assembly further includes an implantable defibrillation device having a pulse generator that provides defibrillation pulses and that is configured to receive the connector to couple the defibrillation electrode to the pulse generator. The device further includes a system that evaluates and conditions the assembly to provide defibrillation therapy to the heart without requiring arrhythmia induction of the heart. The system may condition the device for defibrillation therapy by reforming the defibrillation output capacitor and evaluate defibrillation lead DC resistance, and R wave sensing and detection. In addition, the system may estimate defibrillation thresholds and electrical fields and condition the device by setting the device to provide an output voltage above the estimated threshold. All of the foregoing may be accomplished without inducing ventricular fibrillation.

13 Claims, 9 Drawing Sheets

IMPLANTABLE CARDIAC DEFIBRILLATION ASSEMBLY INCLUDING A SELF-EVALUATION SYSTEM AND METHOD

FIELD OF THE INVENTION

The present invention is generally directed to an implantable cardiac defibrillation assembly including an implantable cardiac defibrillation device (ICD) and lead. The present invention is more particularly directed to such an assembly wherein the device includes a system that evaluates and conditions the assembly to provide defibrillation therapy to a heart without requiring arrhythmia induction of the heart.

BACKGROUND

Implantable cardiac defibrillators (ICD's) are well known in the art. These devices, encapsulated in a conductive housing or enclosure, are generally implanted in a pectoral region of a patient and electrically connected to the heart with one or more electrode carrying leads. One lead includes at least one defibrillation electrode arranged to be positioned in the right ventricle. An arrhythmia detector detects ventricular arrhythmias, such as ventricular fibrillation. When such an arrhythmia is detected, a pulse generator delivers a defibrillating shock from the defibrillation electrode in the right ventricle to the conductive housing to terminate the arrhythmia. Alternatively, such arrhythmia terminating systems may further include another defibrillation electrode arranged to be positioned in the right atrium and electrically connected to the right ventricular defibrillation electrode. In this arrangement, the defibrillating shock is delivered from the parallel connected right ventricular and right atrial electrodes to the conductive housing.

Ventricular fibrillation is an immediately life threatening cardiac arrhythmia. It requires immediate and effective defibrillation therapy. As a result, when an ICD is implanted within a patient, the implant procedure customarily requires intentional induction of ventricular fibrillation and then immediate defibrillation with the newly implanted device. This is performed to test the device and lead system and to confirm that the device is set and capable to provide a shock voltage that is above the required defibrillation threshold (DFT).

The ventricular fibrillation inductions are carried out in a controlled environment and always with external defibrillation back-up. However, with ventricular fibrillation, there is always a mortality risk associated with the procedure. It would of course be advantageous if such a risk could be avoided.

Modern ICDs generally provide more than a sole defibrillation function. For example, ICDs providing single chamber pacing and/or dual chamber pacing therapy, with or without physiologic rate control, are now customarily implanted. In many cases, a therapy other than defibrillation therapy is the intended primary therapy while defibrillation therapy is secondarily provided and made available because, while the patient has not had a ventricular fibrillation episode, the patient's condition or symptoms indicate a potential for the development of the arrhythmia.

As the functionality of ICDs is further extended, it will become more and more likely that an ICD will be implanted for a primary condition other than ventricular fibrillation. As a result, such devices will be more frequently implanted by physicians who are unwilling to induce ventricular fibrillation during the implant procedure. Hence, it would be most desirable if an ICD were capable of being evaluated and conditioned for providing ventricular fibrillation defibrillation therapy during an implant procedure without the need for ventricular fibrillation induction. It would be further advantageous if such evaluation and conditioning could be performed by the device itself and essentially automatically.

SUMMARY

Briefly, what is described herein is an implantable cardiac defibrillation assembly. The assembly includes at least one implantable lead including a defibrillation electrode adapted for placement in a chamber of the heart and including a connector, and an implantable defibrillation device having a pulse generator that provides defibrillation pulses and that is configured to receive the connector to couple the defibrillation electrode to the pulse generator. The device further includes a system that evaluates and conditions the assembly to provide defibrillation therapy to the heart without requiring arrhythmia induction of the heart.

The at least one implantable lead has a lead DC resistance between the connector and the defibrillation electrode. The assembly may include a DC resistance measuring circuit that measures the lead DC resistance responsive to the device receiving the connector coupling the defibrillation electrode to the pulse generator. A display may then display the measured lead DC resistance. The assembly may alternatively or in addition include an alarm that provides a perceptible indication when the lead DC resistance is outside of a predetermined DC resistance range.

The assembly may further include a ventricular sensing electrode that senses ventricular electrical activity including R waves of the heart and the device may include a ventricular sensing circuit that is adapted to be coupled to the ventricular sensing electrode to sense the ventricular activity sensed by the ventricular sensing electrode. The system may further include a confirmation circuit that confirms that the sensing ventricular electrode and ventricular sensing circuit are able to sense R waves of the heart. The confirmation circuit preferably confirms acceptable R wave amplitude and/or slew rate.

The assembly may further include an atrial sensing electrode that senses atrial activity including P waves of the heart and the device may include an atrial sensing circuit that is adapted to be coupled to the atrial sensing electrode to sense the atrial activity sensed by the atrial sensing electrode. The confirmation circuit may then confirm sensing of an R wave corresponding to each sensed P wave. When the device includes a dual chamber pacer, a relatively long AV delay may be set to enable sensing of conducted R waves. When the device includes a single chamber pacer, a relatively long escape interval may be set to enable sensing of the R waves. Alternatively, the assembly may include an R wave generator that generates synthetic R waves for sensing by the ventricular sensing electrode and the ventricular sensing circuit. The device may include a pacing pulse generator that generates the synthetic R waves or an external pulse generator with surface electrodes may generate the synthetic R waves. The assembly may further include a correlation circuit that correlates each generated synthetic R wave with a sensed synthetic R wave. As a further alternative, the assembly may include an atrial pacing electrode, and the device may include an atrial pulse generator that provides the atrial pacing electrode with atrial pacing pulses to induce conducted R waves. The confirmation circuit may then confirm sensing of the conducted R waves by the ventricular sensing electrode and the ventricular sensing circuit.

The system may further include a defibrillation threshold estimating circuit that estimates defibrillation threshold. The estimating circuit may set the pulse generator to a defibrillation voltage above the estimated threshold.

The device may include a ventricular pacing pulse generator that provides ventricular pacing pulses and the assembly may further include near-field and far-field pacing electrode configurations. The estimating circuit may then measure near-field and far-field pacing thresholds to estimate defibrillation threshold.

The device may include a conductive enclosure. The estimating circuit may cause the pulse generator to apply a test pulse of a given voltage between the device enclosure and the defibrillation electrode and the estimating circuit may then measure an induced voltage induced by the test pulse and indicative of a corresponding defibrillation electrical field. The assembly may include a ventricular sensing electrode distal to the defibrillation electrode and the estimating circuit may measure the induced voltage between the defibrillation electrode and the ventricular sensing electrode. The at least one lead may include the defibrillation electrode and the ventricular sensing electrode.

The defibrillation threshold estimating circuit may perform a plurality of differed threshold estimates and thereafter compute a threshold average from the plurality of estimates. Further, the estimating circuit may cause the pulse generator to deliver a test defibrillation pulse during a T wave. An arrhythmia detector may then determine if the test defibrillation pulse induced an accelerated arrhythmia of the heart as a final defibrillation threshold test.

Also disclosed herein is a defibrillation lead assembly including a defibrillation lead including a connector and at least one defibrillation electrode coupled to the connector, a sealed enclosure enclosing the defibrillation lead, a first conductor coupled to the connector and extending through the sealed enclosure, and a second conductor coupled to the defibrillation electrode and extending through the sealed enclosure. The first and second conductors may be used to measure the DC resistance between the defibrillation electrode and the connector.

Also disclosed herein is an implantable cardiac defibrillation assembly including implantable lead means including a defibrillation electrode for making electrical contact with a chamber of the heart and including a connector, and device means having pulse generating means for providing defibrillation pulses and being configured for receiving the connector for coupling the defibrillation electrode to the pulse generating means. The device means further includes qualifying means for evaluating and conditioning the assembly to provide defibrillation therapy to the heart without requiring arrhythmia induction of the heart.

Also disclosed herein is a method for use in an implantable cardiac stimulation device during a procedure of implanting a cardiac defibrillation assembly including the device. The method includes the steps of providing at least one implantable lead including a defibrillation electrode adapted for placement in a chamber of the heart and including a connector, providing an implantable defibrillation device having a pulse generator that provides defibrillation pulses and that is configured to receive the connector to couple the defibrillation electrode to the pulse generator, evaluating the assembly with the device to determine suitability for implanting the assembly and conditioning the assembly with the device to provide defibrillation therapy to the heart. The evaluating and conditioning steps are performed within the device without inducing an accelerated arrhythmia of the heart.

Also disclosed herein is a subcutaneous cardiac defibrillation assembly. The assembly comprises at least a pair of defibrillation electrodes adapted for placement within a patient's body outside the patient's heart, a defibrillation device placeable within the patient that provides test and defibrillation pulses between the defibrillation electrodes, and a monitor separate from the defibrillation device. The monitor includes electrodes implantable within the heart that measures an electric field within the heart resulting from a test pulse applied by the defibrillation device to the heart.

Also disclosed herein is a method for use in a procedure of implanting a cardiac defibrillation assembly. The method comprises placing at least two defibrillation electrodes within a patient's body outside of the patient's heart, placing a defibrillation device having a pulse generator that provides defibrillation and test pulses within the patient's body, connecting the defibrillation electrodes to the pulse generator, applying a test pulse between the defibrillation electrodes, and measuring an electric field within the heart resulting from the test pulse.

BRIEF DESCRIPTION OF THE DRAWINGS

Further features and advantages may be more readily understood by reference to the following description taken in conjunction with the accompanying drawings, in which.

DESCRIPTION OF THE PREFERRED EMBODIMENTS

The following description is of the best mode presently contemplated. This description is not to be taken in a limiting sense but is made merely for the purpose of describing the general principles of the illustrative embodiments.

The scope of the invention should be ascertained with reference to the issued claims. In the description that follows, like numerals or reference designators will be used to refer to like parts or elements throughout.

Figure 1:
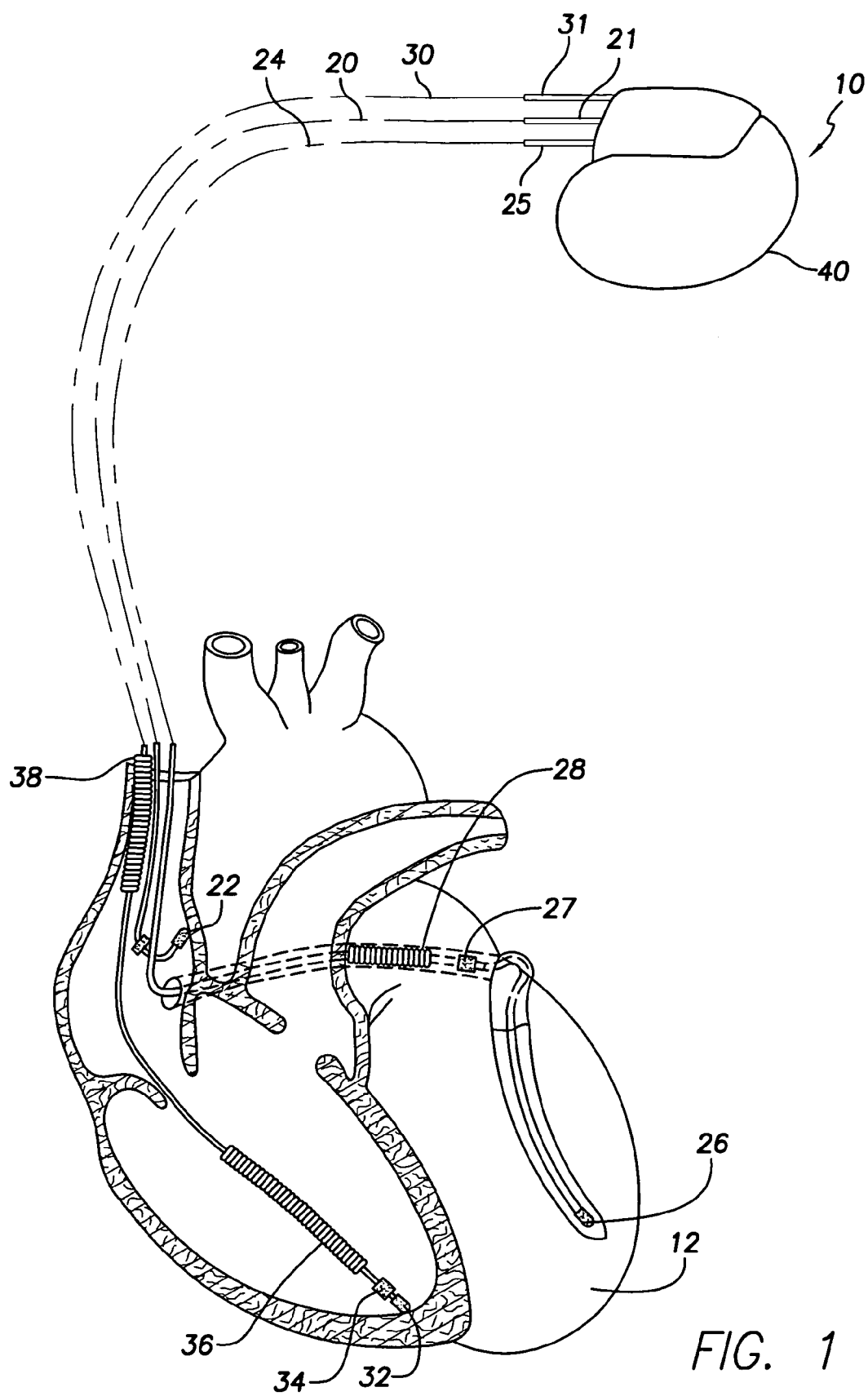
FIG. 1 is a simplified diagram illustrating an implantable cardiac defibrillation assembly embodying one illustrative embodiment and including an implantable cardiac stimulation device having defibrillation capability and a lead system including three leads implanted into a patient's heart for delivering multi-chamber pacing and defibrillation therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 by a lead connector 21. The lead 20 has at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 by a lead connector 25. The lead 24 is designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30. In this embodiment, the lead 30 includes a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
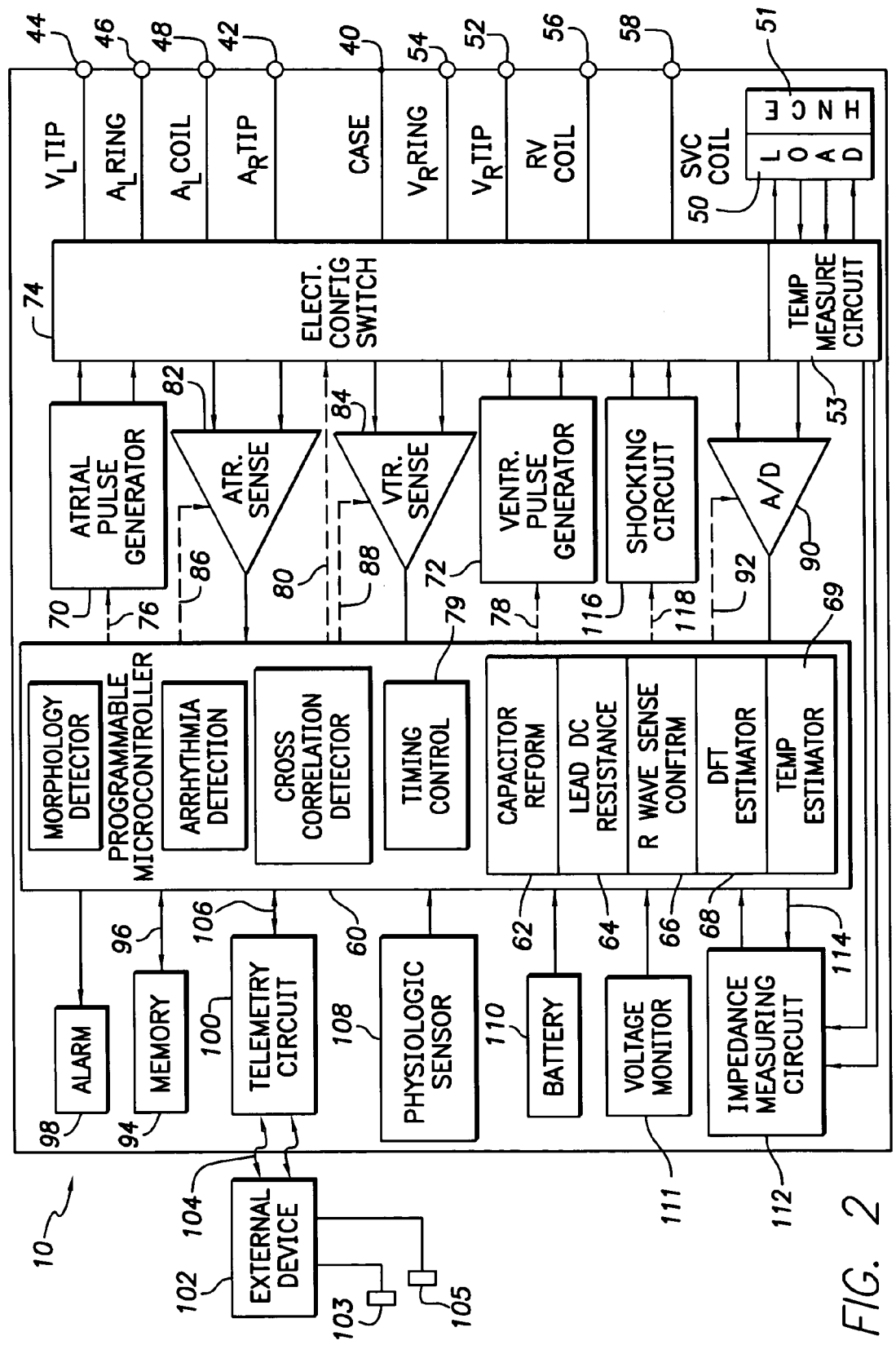
FIG. 2 is a functional block diagram of the implantable stimulation device illustrating the basic elements thereof for providing cardioversion, defibrillation and pacing stimulation in four chambers of the heart and defibrillation therapy evaluation and conditioning embodying one illustrative embodiment.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown in FIG. 1 and schematically in FIG. 2, is often referred to as the "can", "case" or "case electrode" and may be programmably selected to act as a return electrode for all "unipolar" pacing modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, escape interval, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Lithium/silver vanadium oxide batteries have been found to be suitable for these purposes.

As further shown in FIG. 2, the device 10 is shown as having an impedance measuring circuit 112 which is enabled by the microcontroller 60 via a control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrodes may be used.

In the case where the therapy to be provided by the stimulation device 10 is intended to include cardioversion and/or defibrillation, the device must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

In accordance with one illustrative embodiment, the device 10 is capable of being evaluated and conditioned for providing defibrillation therapy during implant without requiring induction of fibrillation. To that end, and in accordance with this embodiment, the device is capable of reforming the output capacitor of the shocking circuit 116, evaluating the output shock voltage magnitude, measuring shock lead DC resistance, confirming R wave sensing, estimating defibrillation threshold (DFT), and programming an output shock voltage above the estimated DFT. By performing these functions, the device 10 may be readied during implant for providing defibrillation therapy without fibrillation induction.

Figure 3:
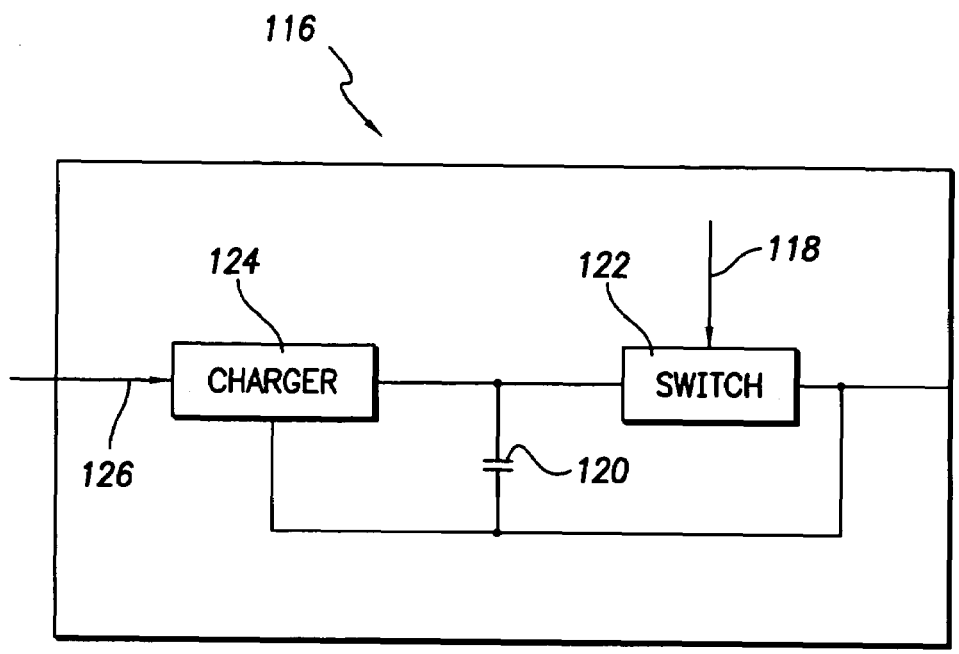
FIG. 3 is a simplified block diagram of the shocking circuit of the device of FIG. 2.

The reforming of the output capacitor of the shocking circuit 116 is controlled by a capacitor reform stage 62 of the micro-controller 60 under control from operating instructions stored in the memory 94. As may be seen in FIG. 3, the shocking circuit 116 includes the output capacitor 120 which provides a defibrillation shock to the electrode configuration programmably selected by the switch 74. A discharge switch 122 initiates the discharge under control of the control signal 118. A charger 124 which is coupled to the battery 110 charges the capacitor 120 under control of a charge control signal 126 provided by the capacitor reform stage 62. The manner in which the capacitor is reformed is described in greater detail hereinafter with respect to the subroutine flow chart of FIG. 5.

Once the capacitor 120 is fully charged, the capacitor voltage is measured by a voltage monitor 111 to determine its sufficiency for defibrillation. If the charged voltage is below a predetermined charged voltage, an alarm 98 provides a perceptible indication.

The sufficiency of the energy stored for defibrillation may also be determined by discharging the capacitor 120 into a resistive load 50 selected by the switch 74. In intimate thermal contact with the resistive load 50 is an element 51 made of a ceramic or metallic substrate or any other suitable element having a relatively high thermal heat capacity (HHCE) 51. Hence, when the capacitor 120 is discharged into the resistive load 50, the resistive load and the high heat capacity element 51 which is in thermal equilibrium with the resistive load will increase in temperature. A temperature measuring circuit 53 measures the temperature of the element 51. The degree of temperature increase is proportional to the amount of electrical energy that was discharged from the capacitor and hence, the processor 60 may include a temperature estimator 69 to estimate a measure of the energy stored in the capacitor. Embedded in the element composed of the resistor 50 and the high heat capacity element 51 is a temperature sensing element such as a thermistor or a diode. Such temperature sensing elements are well known in the art.

The next evaluation to be made by the device 10 during the implant procedure is the measurement of the DC resistance of the defibrillation lead 30. To that end, the lead DC resistance is measured by a lead DC resistance stage 64 of the microcontroller 60. This is also described subsequently in detail with respect to the subroutine flow chart of FIG. 6.

The next evaluation to be made by the device 10 during implant is to confirm R wave sensing. This is implemented by an R wave sense confirmation stage 66 as more fully described with respect to the subroutine flow chart of FIG. 7. In accordance with one embodiment, R wave sensing may be confirmed by the generation of synthetic R waves. As will be seen subsequently, the synthetic R waves may be generated by the device 10, or by the external device 102. To that end, the external device 102 includes surface electrodes 103 and 105 which may be attached to the skin of the patient's chest.

The last evaluation to be made during implant is an estimation of defibrillation threshold (DFT) and the programming of the device to provide a shock voltage in excess of the estimated DFT. To this end, the device includes a DFT estimator stage 68 of the microcontroller 60, the operation of which is described in detail with respect to the subroutine flow chart of FIG. 8.

Figure 4:
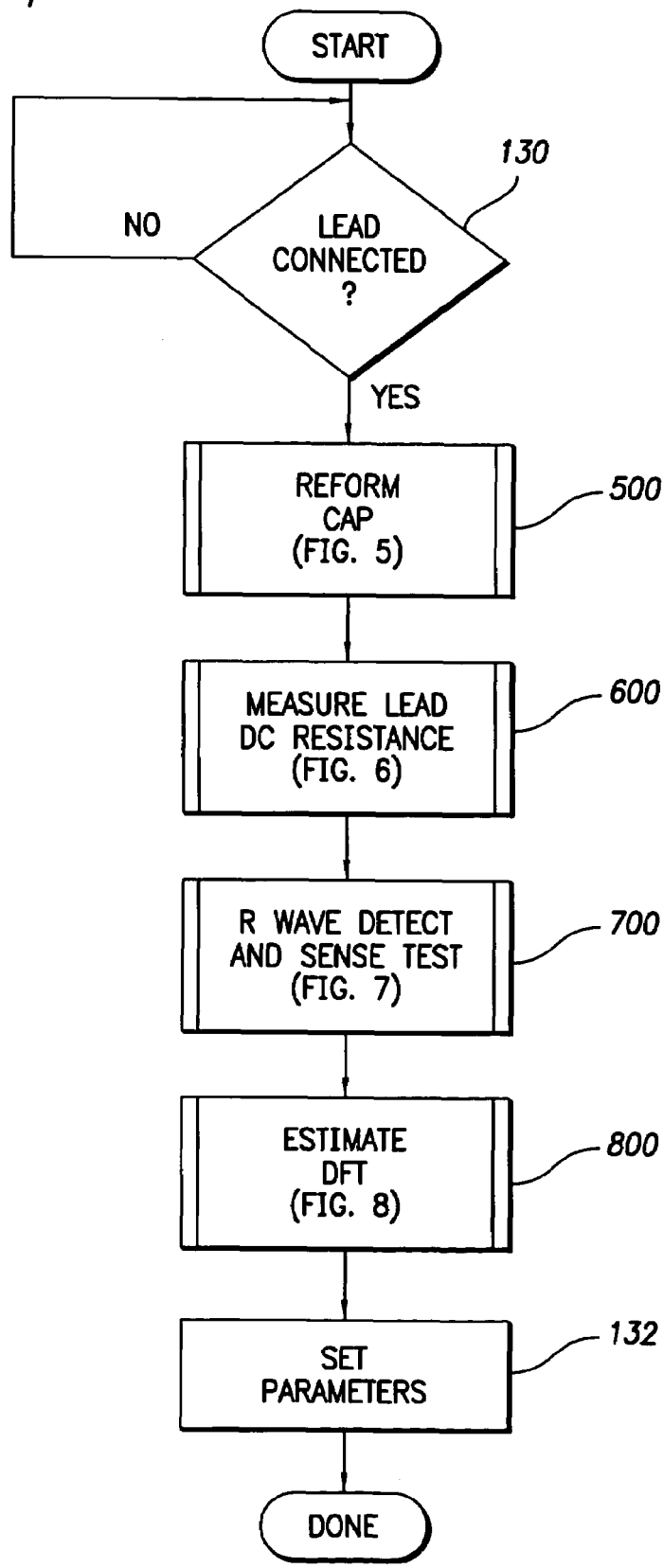
FIG. 4 is a flow chart describing an overview of the operation of one embodiment.

In FIG. 4, a flow chart is shown describing an overview of the operation and novel features implemented in one embodiment of the device 10. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The evaluation and conditioning of the device for providing defibrillation therapy in accordance with this embodiment initiates when the defibrillation lead, as for example, lead 30 is connected to the device 10 by the insertion of its connector 31 into the device. This is represented by decision block 130 wherein the device determines if the defibrillation lead has been connected to the device. If the lead has been connected to the device, the process then advances to subroutine block 500 for reforming the output capacitor of the defibrillator. As will be seen hereinafter with respect to the detailed description of the capacitor reforming subroutine flow chart of FIG. 5, the output capacitor of the shocking circuit is preferably charged to a maximum voltage. The charge time is measured and an alarm is provided if the charge time is too long. Also, the charged voltage is measured and an alarm is provided if the charged voltage is below a predetermined charged voltage. Finally, the capacitor reforming subroutine is completed when the output capacitor is discharged into a resistive load. A voltage indicator associated with the resistive load may then be observed for indicating the magnitude of the charged voltage.

Once the capacitor reforming subroutine is performed, the process then advances to a lead DC resistance measurement subroutine block 600. The subroutine 600 is more particularly described with respect to the flow chart of FIG. 6. During the subroutine 600, the DC resistance of the defibrillation lead is measured and an alarm is provided if the DC resistance of the lead is outside of predetermined resistance limits. Also, the value of the DC resistance may be displayed on the external device 102.

Once the lead DC resistance measurement subroutine 600 is completed, the process then advances to a subroutine block 700 wherein a test is performed to confirm R wave sensing and detection. The subroutine 700 is more particularly described hereinafter with reference to FIG. 7. As will be seen hereinafter, the subroutine 700 accommodates long rhythms, dual chamber sensing, and single chamber sensing conditions. For each condition, R wave magnitudes and slew rates are measured with appropriate alarms being provided should either the R wave amplitudes or slew rates be insufficient.

Once the test to confirm R wave sensing and detection is completed, the process then advances to subroutine block 800 wherein the defibrillation threshold (DFT) is estimated. The DFT estimation subroutine 800 is described in detail hereinafter with reference to the flow chart of FIG. 8. As will be seen, the device 10 performs a plurality of different DFT estimates and may utilize any one of the estimates or an average of the estimates to complete the DFT estimation.

Once the DFT estimation subroutine is completed, the process then advances to activity block 132 wherein appropriate parameters for defibrillation are automatically programmed into the device. Among the parameters to be programmed in accordance with the activity block 132 is the output voltage of the shocking circuit. In accordance with this embodiment, the charging voltage of the output capacitor is selected so as to be greater than the estimated defibrillation threshold. Once the various parameters are programmed, the process completes.

Figure 5:
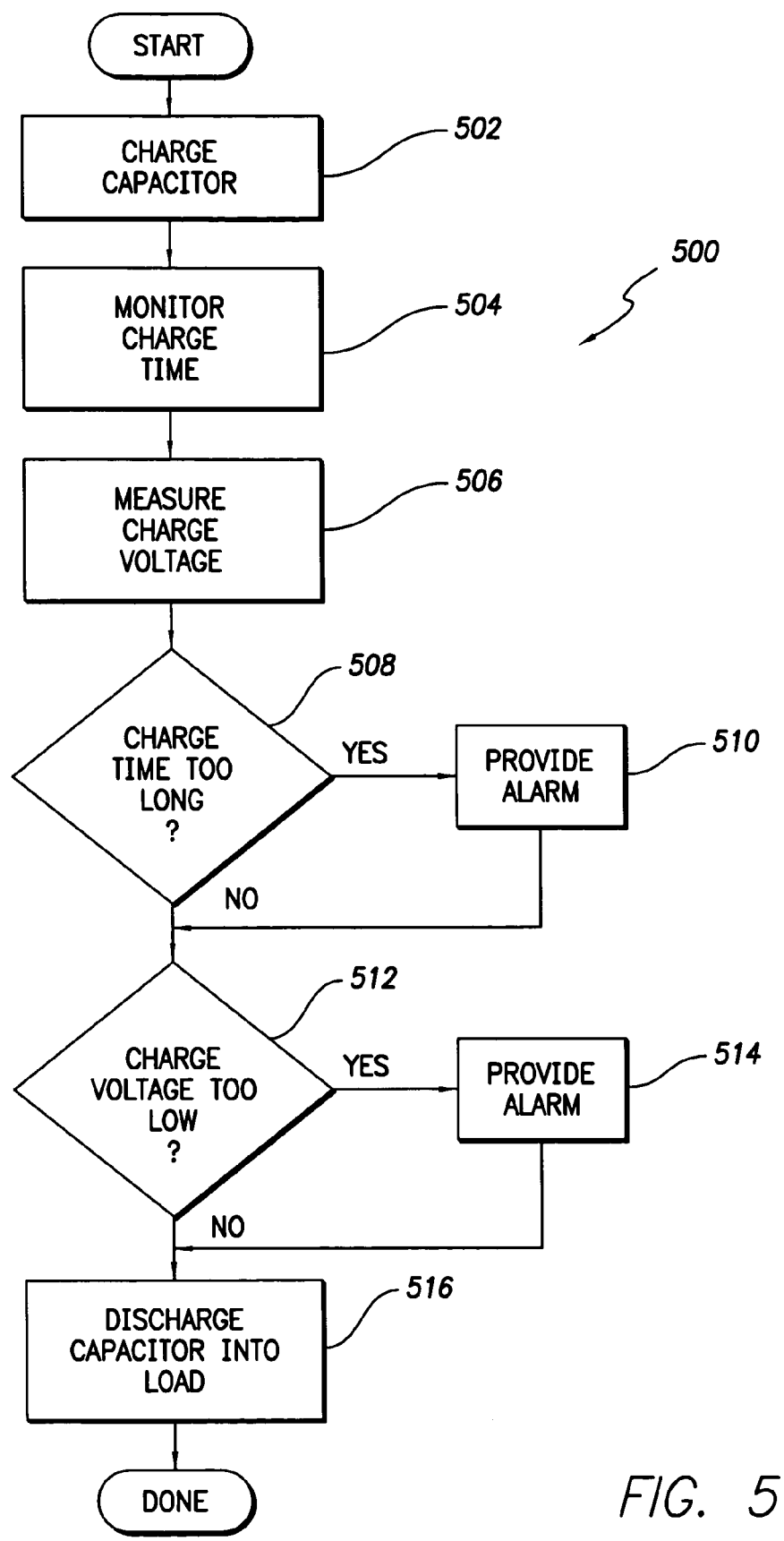
FIG. 5 is a flow chart describing the capacitor reforming subroutine of FIG. 4.

Referring now to FIG. 5, it shows the flow chart of the capacitor reforming subroutine 500 of FIG. 4. The subroutine initiates at activity block 502 wherein the capacitor reform stage causes the charger 124 (FIG. 3) to charge the output defibrillation capacitor 120. Once charging has begun, the process advances to activity block 504 wherein the charging time is timed by, for example, the timing control 79. When the capacitor is fully charged, the process advances to activity block 506 wherein the charged voltage on the capacitor is measured. When the charged voltage on the capacitor 120 is measured, the process advances to decision block 508 wherein it is determined if the charge time is greater than a predetermined charge time. If it took longer to charge the capacitor 120 than the predetermined charge time, the process then advances to activity block 510 wherein an alarm is provided. Here, the capacitor reform stage 62 causes the alarm 98 to provide a perceptible alarm indicating that the charge time took too long. The alarm 98 may provide an audible sound so as to be heard by the implanting physician.

If the charge time is below the predetermined charge time, the process advances from decision block 508 to decision block 512 wherein it is determined if the charged voltage is below a predetermined charge voltage. If the charged voltage is below a predetermined charge voltage, the process immediately advances to activity block 514 wherein the alarm 98 provides a second perceptible alarm indicating that the charge voltage fell below the predetermined charge voltage. If the charge voltage is not below the predetermined charge voltage, the process then advances to activity block 514 wherein the capacitor reform stage 62 causes the switch 122 of the shocking circuit 116 and the electrode configuration switch 74 to discharge the capacitor 120 into the resistive load 50. In doing so, the resistive load 50 will heat to a temperature and cause the liquid crystal 51 to change color at which time the color of the liquid crystal 51 may be discerned by the implanting physician to provide an additional indication of the charged voltage on the capacitor 120. After the capacitor has discharged in accordance with activity block 514, the subroutine completes.

Figure 6:
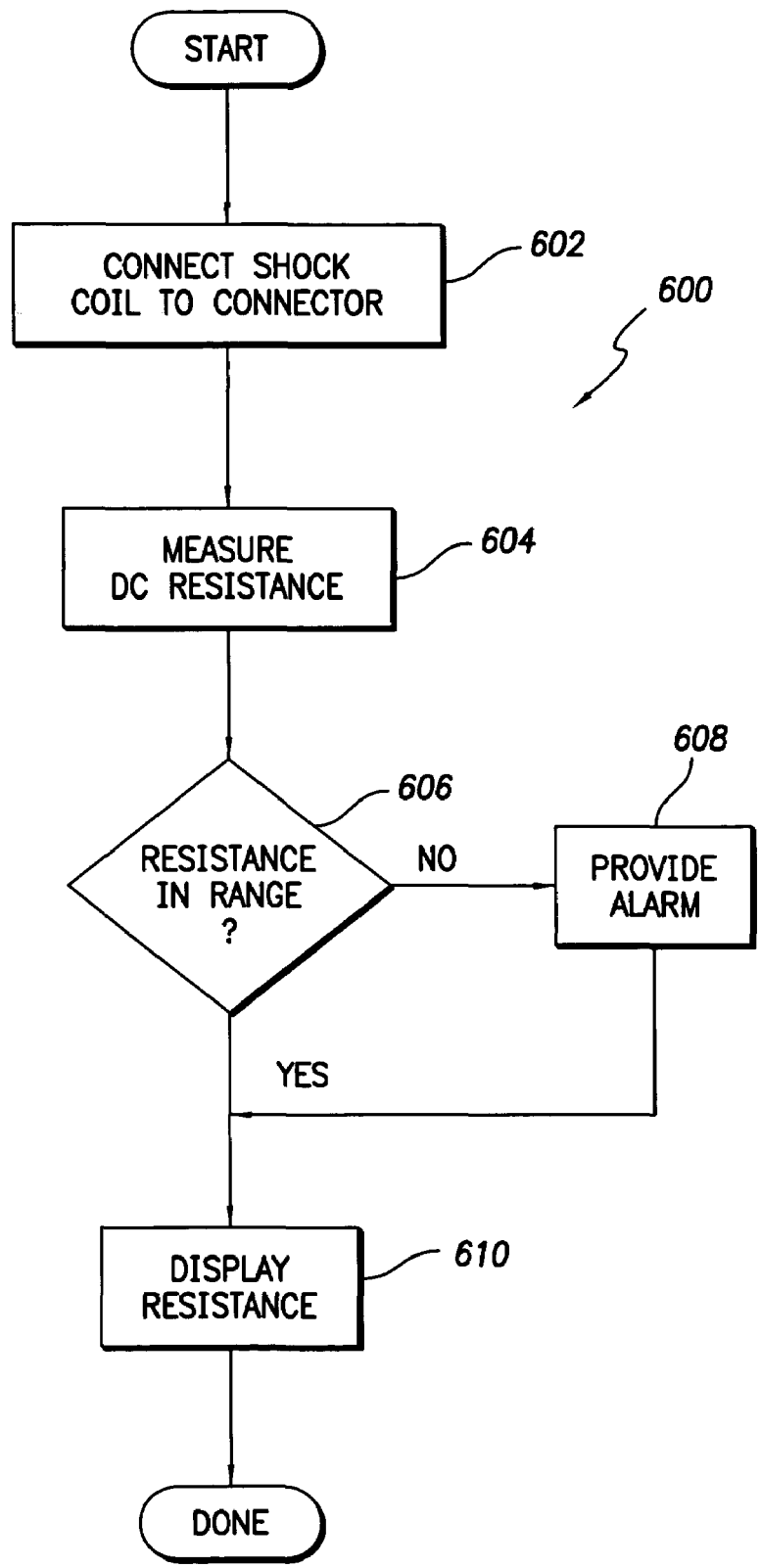
FIG. 6 is a flow chart describing the lead DC resistance measurement subroutine of FIG. 4.

Referring to FIG. 6, it shows the lead DC resistance measurement subroutine 600. The lead DC resistance measurement subroutine initiates at activity block 602 wherein the lead DC resistance stage 64 connects between the contact of connector 31 of lead 30 which couples to, for example, the right ventricular shock coil 36, and the shock coil 36. After the connection is made in accordance with activity block 602, the process advances to activity block 604 wherein the lead DC resistance stage 64 measures the DC resistance of the lead 30 between the connector 31 and the defibrillation shock coil 36. The process then advances to decision block 606 wherein it is determined if the resistance is within a given range. The given range may be, for example, 50–200 ohms. If the resistance falls outside of the given range, the process advances to activity block 608 wherein the alarm 98 provides a third perceptible indication as an alarm indicating that the resistance of the defibrillation lead is outside of the given range. However, if the DC resistance of the lead 30 is within the given range, the process then advances to activity block 610 wherein the DC resistance of the lead is displayed. In carrying out activity block 610, the lead DC resistance stage 64 may provide the measured resistance to the telemetry circuit 108 which then transmits the measured resistance to the external device 102 for display. After the measured lead DC resistance is displayed, the process completes.

Figure 7:
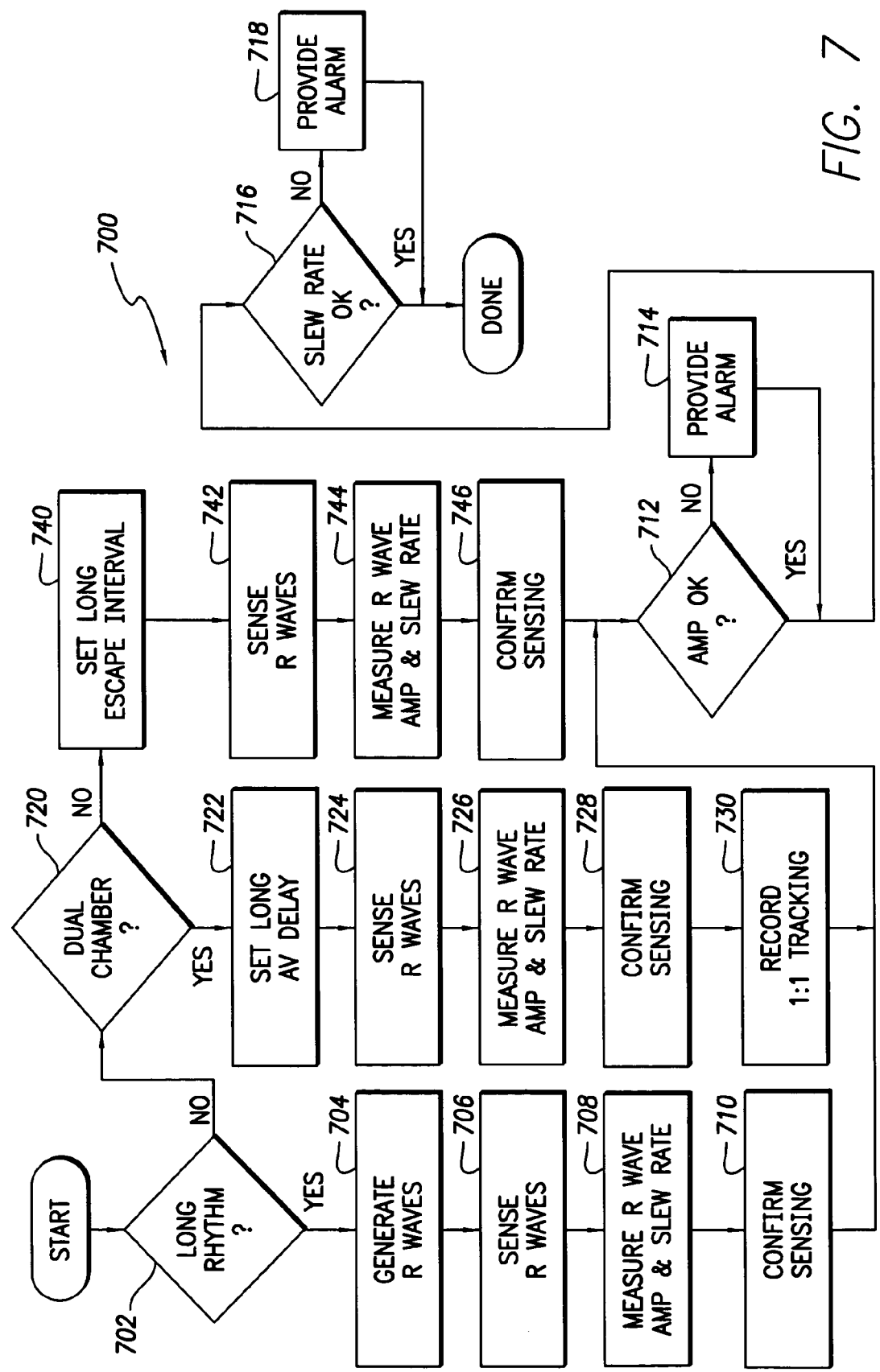
FIG. 7 is a flow chart describing the R wave detection confirmation subroutine of FIG. 4.

Referring now to FIG. 7, it shows a flow chart of the subroutine 700 for confirming R wave sensing and detection. For sensing and detecting R waves to support arrhythmia detection, the device may sense ventricular activity between the distal sensing/pacing electrode 32 of lead 30 and the shock coil 36 of lead 30 or between the electrode 32 and the device case 40. However, sensing between electrode 32 and shock coil 36 may be preferred as this permits the sensing of localized ventricular activity.

The subroutine 700 initiates at a decision block 702 wherein the R wave sense and detect confirmation stage 66 determines if the patent has a long rhythm. A long rhythm may be defined as one wherein the intrinsic R waves of the heart occur at a rate of 30 beats per minute or less. If this is the case, the subroutine advances to activity block 704 to generate synthetic R waves. Activity block 704 may be carried out in three different ways for generating synthetic R waves. A first synthetic R wave generation method may include the generation of repetitive electrical pulses between either the SVC shock coil 38 and the case 40 or the right ventricular shock coil 36 and the case 40. The repetitive pulses may be provided by the ventricular pulse generator 72 and have an amplitude of, for example, 5 mV and a repetition rate of 50 pulses per minute. The repetitive pulses may then be sensed in accordance with activity block 706 as R waves.

A second procedure for generating synthetic R waves may include the use of the external device 102. Here, the surface electrodes 103 and 105 are placed on the patient's chest and repetitive pulses are applied by the external device 102 between the electrodes 103 and 105. These repetitive pulses may then be detected in activity block 706 as R waves.

A last procedure for generating synthetic R waves may include pacing the atria as for example with the atrial pulse generator 78 applying pacing pulses between the right atrial distal electrode 22 and the case 40 of the device 10. The atrial pacing pulses then induce conducted R waves which then may be sensed in accordance with activity block 706.

After the sensing of the synthetic R waves, the process advances to activity block 708 wherein the amplitude and slew rate of the sensed R waves are measured. After the amplitude and slew rates of the sensed R waves are measured in accordance with activity block 708, the process advances to activity block 710 wherein the R wave sensing and detection is confirmed. In implementing activity block 710, the R wave sense confirmation stage 66 may operate in concert with the external device 102. In doing so, the external device 102 may also record sensed synthetic R waves or synthetic R waves which it produces so that the R wave sense confirmation stage 66 may correlate the recordings of the external device with its own sensing record to confirm the detection of the synthetic R waves.

Upon completion of activity block 710, the process then advances to decision block 712. In decision block 712, the confirmation stage 66 determines if the amplitudes of the sensed R waves are above a given minimum amplitude. If they are not, the process advances to activity block 714 wherein the alarm 98 provides a perceptible indication that the R wave amplitudes are not above the predetermined minimum level. However, if the amplitudes of the sensed R waves are above a minimum level, the process advances to decision block 716 wherein it is determined if the slew rate of the sensed R waves is above a predetermined minimum slew rate. If it is not, the process advances to activity block 718 wherein the alarm 98 provides a perceptible alarm of that condition. However, if the slew rates of the sensed R waves are acceptable, the process completes. Decision blocks 712 and 716 are provided to assure that the sensing circuits for supporting arrhythmia detection are operating properly.

If in decision block 702 it is determined that there is not a long rhythm, the process then advances to decision block 720 to determine if the device has been programmed for dual chamber pacing. If the device has been programmed for dual chamber pacing, the confirmation stage 66 in activity block 722 sets a long AV delay to support the sensing of normally conducted R waves. After the AV delay is established in accordance with activity block 722, the process advances to activity block 724 wherein the ventricular sensing circuits 84 sense the normally conducted R waves. Then, the process advances to activity block 726 wherein the amplitudes and slew rates of the sensed R waves are measured. After measurement of the amplitudes and slew rates of the sensed R waves, the process advances to activity block 728 wherein R wave sensing is confirmed. This confirmation may be made, as previously described, in concert with the sensing of the R waves by the external device 102.

Following activity block 728, the process then advances to activity block 730. Here, it is determined if one-to-one tracking was recorded. Because the device is programmed for dual chamber pacing, the atrial sensing circuit 82 will also be activated for sensing P waves of the heart. In activity block 730 therefore, the confirmation stage 66 confirms the sensing of an R wave corresponding to each sensed P wave. After one-to-one tracking has been confirmed, the process then advances to decision blocks 712 and 716 to confirm operation of the ventricular sensing circuit 84 with respect to R wave amplitude and slew rate.

If in decision block 720 it is determined that the device is not set for dual chamber pacing, the confirmation stage 66 then knows that the device is set for single chamber pacing. As a result, the process advances to activity block 740 wherein the confirmation stage 66 sets a long escape interval to support sensing of intrinsic R waves. Once the long escape interval has been set, the confirmation stage 66 causes the ventricular sense circuit 84 to sense R waves in accordance with activity block 742. The process then advances to activity block 744 where once again the amplitudes and slew rates of the sensed R waves are measured. Once the amplitude and slew rates of the sensed R waves are measured, the process advances to activity block 746 where the R wave sensing is confirmed. Activity block 746 may be carried out in the same manner as activity block 728 previously described.

Once the R wave sensing is confirmed in accordance with activity block 746, the process then advances to determine proper operation of the ventricular sense circuit. As previously described, this is done by performing decision block 712 for amplitude and decision block 716 for slew rate and providing appropriate alarms when necessary. The subroutine then completes.

Figure 8:
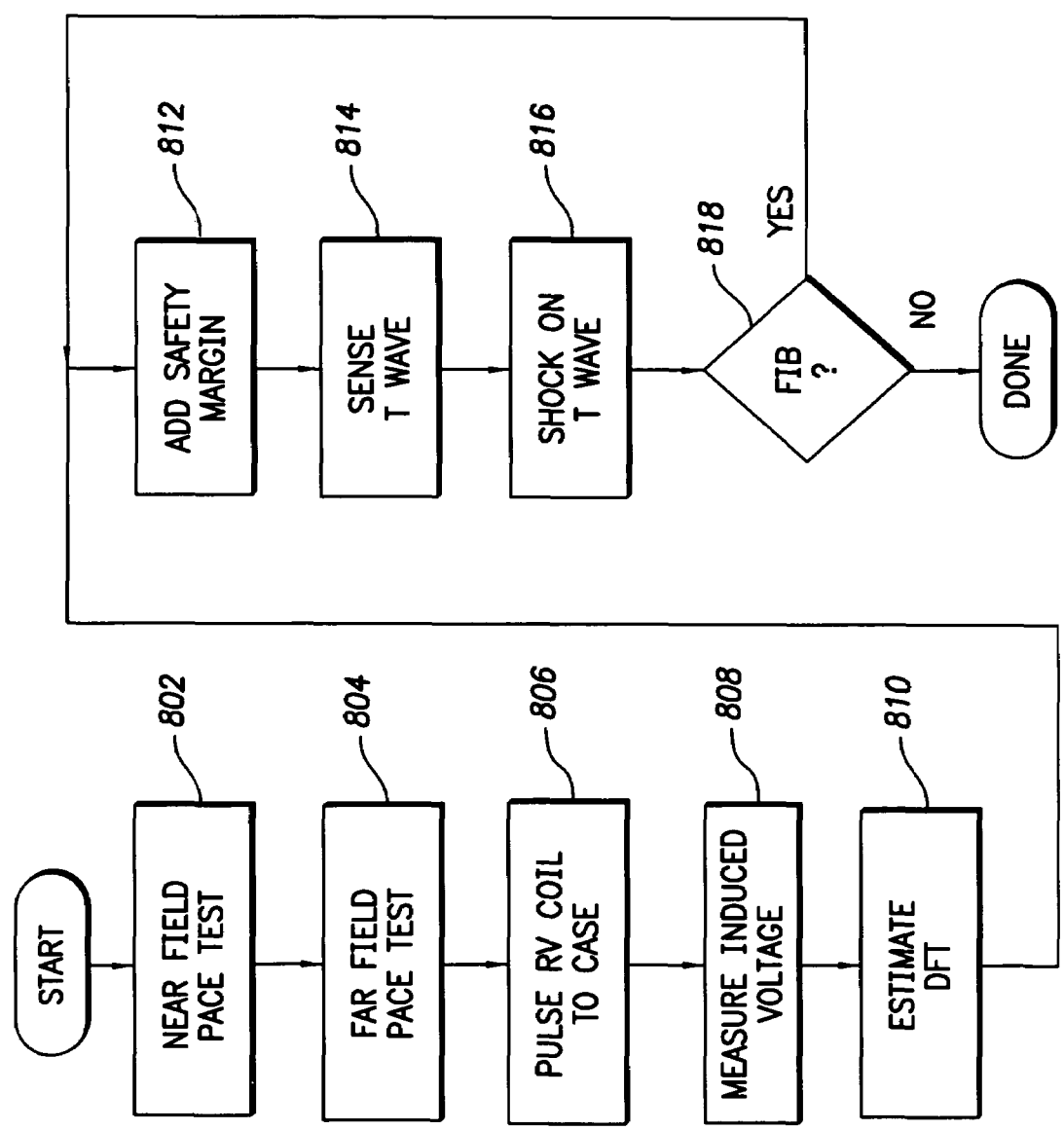
FIG. 8 is a flow chart describing the defibrillation threshold estimation subroutine of FIG. 4.

Setting the defibrillation threshold (DFT) on a device consists of two steps. The first step is an estimation of the DFT. The second is the verification on the DFT. FIG. 8 is a flow diagram of subroutine 800 of FIG. 4 for DFT estimation and optional DFT confirmation. The subroutine initiates at activity block 802. Here, the device 10 performs a near field pacing threshold test for the right ventricle. More specifically, the ventricular pulse generator 72 provides pacing pulses between the distal tip electrode 32 and the shock coil 36 to determine a near field pacing threshold. Once the near field pacing threshold test is completed, the process advances to activity block 804 wherein a far field pacing threshold test is performed. Here, the ventricular pulse generator 72 applies pacing pulses between the right ventricular shock coil 36 and the case 40 of the device 10. Both the near field pacing threshold and the far field pacing threshold provide an estimate of the defibrillation threshold.

The pacing threshold may be determined using any of the well known pacing capture threshold tests known in the art. The estimate, for defibrillation energy, is generally 10 joules plus two times the pacing energy (in joules) required to capture the ventricles. More particularly, the defibrillation energy may be determined by the following expression:

$$DFT(J)=10.1+(2.2VCT(J))$$

where DFT(J) is the required defibrillation energy (threshold)

and

VCT(J) is the energy required to capture the ventricles.

In terms of required defibrillation voltage, the following expression may be used:

$$DFT(V)=453\times(38VCT(V)^2)$$

where DFT(V) is the required defibrillation voltage (threshold)

and

VCT(V) is the voltage required to capture the ventricles.

For a more detailed discussion, reference may be had to "Capture Threshold Correlates With Defibrillation Threshold", by J E Val-Mejias, et al, published in Europace 2001, pp. 595-600.

Following activity block 804, the process advances to activity block 806. In accordance with activity block 806, a test pulse (e.g. 1 volts) is applied between the right ventricular coil electrode 36 and the case 40 of the device 10. This causes a voltage to be induced between the tip electrode 32 (which is in the apex) and the coil electrode 36 which is indicative of a corresponding defibrillation electrical field.

This induced voltage is measured in accordance with activity block 808. A first order estimate of this electric field is the measured voltage between the tip electrode 32 and coil electrode 36 divided by the distance between the electrodes. As an example let's assume that the measured induced voltage was 60 mV. Let us also assume that the distance between the electrodes 32 and 36 is 2 cm. Then as a result of the 1 volt test pulse, we measure an electric field in the Apex of (60 mV/2 cm) or 30 mV/cm.

The Apical area is a low electric field region during defibrillation. A minimum electric field of 5–7 V/cm is required to defibrillate the heart during a defibrillation pulse. Still further, the electric field distribution in the thorax during defibrillation of the heart substantially follows linear system theory. (See for example Wharton et al., Circulation 1992 April; 85(4): 1510-23).

Therefore, to achieve about 7 V/cm at the apex, the test pulse between the coil and case must be scaled by 7000/30 or 233 times. Also considering that the defibrillation waveform is a truncated exponential of a duration of approximately 1 time constant, the peak value must be 1.59 the desired average value. This results in an estimated DFT of 1×233×1.59=370V. By the definition of the DFT, a 370V pulse would have 50% probability of converting ventricular fibrillation (VF). Hence a safety margin is added, nominally 100V, to increase the probability of conversion of the first defibrillation shock to greater than 90%.

Following activity block 808, the process advances to activity block 810 where the DFT is estimated. Here the estimated DFT may be based upon the near field threshold test, the far field threshold test, the measured induced voltage, or an average of each of these defibrillation threshold estimates. Once the defibrillation threshold is estimated, the subroutine advances to activity block 812 where a safety margin is added to the estimated DFT in a manner known in the art to arrive at a final DFT estimate.

Upon completion of activity block 812, the process may complete or advance to activity block 814. Activity block 814 and the following activity block 816 may be optional and employed by physicians who desire to perform an additional validation of the DFT estimate. The upper limit of vulnerability (ULV) may be used for the DFT validation as described, for example, in Chen et al., U.S. Pat. No. 5,564,422 which issued on Oct. 5, 1996 and which is incorporated herein by reference. After the physician adds the desired safety margin to the DFT estimate in accordance with activity block 812, the validation process may advance to activity block 814 wherein a T wave of the heart is sensed during normal sinus rhythm. In the following activity block 816, a defibrillation shock is applied during the sensed T wave coincident with normal sinus rhythm. Then, in decision block 818 it is determined if the applied shock induced fibrillation. If it did not, the physician will be assured that the device is set to provide sufficient defibrillation shock output, because the set output exceeds the ULV. The process may then complete. Activity blocks 814 and 816 should only be carried out in a controlled implant environment where external defibrillation hardware is immediately available. If in decision block 818 it is determined that the applied shock did induce fibrillation, then the process returns to activity block 812 where an additional safety margin is added and this process repeated until a shock fails to induce fibrillation.

As previously noted with respect to FIG. 4, once the subroutine of FIG. 8 is completed, the process returns for setting the parameters in the device for defibrillation therapy. This includes, for example, setting the defibrillation output for fibrillation therapy to a level which exceeds the estimated threshold. It will be noted, that the device is now evaluated and conditioned for defibrillation therapy without or minimal need of inducing fibrillation.

Figure 9:
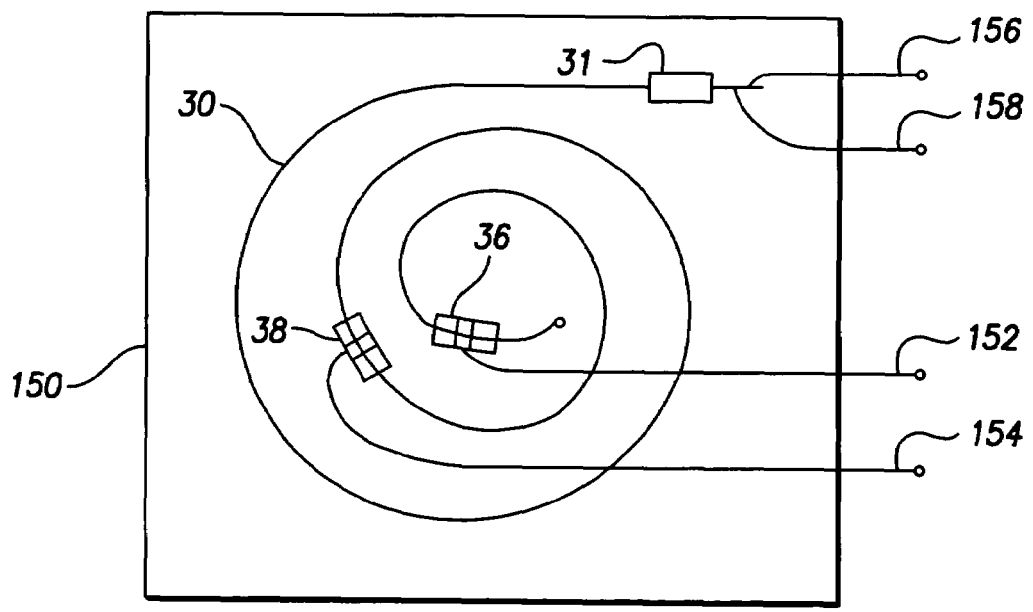
FIG. 9 is a plan view of a defibrillation lead sealed in packaging with wires projecting therefrom to facilitate lead DC resistance measurement in accordance with an alternative embodiment.

Referring now to FIG. 9, it is a plan view of the defibrillation lead 30 sealed in its packaging 150 in a manner which allows the DC resistance of a lead 30 to be determined prior to implant. Here, it is will be noted that a wire 152 is coupled to the defibrillation shock coil 36 and extends sealingly through the perimeter of the package 150. Similarly, another wire 154 is coupled to the SVC coil electrode 38 and sealingly extends beyond the perimeter of the package 150 as well. Also, wires 156 and 158 also extend from the perimeter of the package 150 and are coupled to the contact of the connector 31 which contact the right ventricular coil electrode 36 and the SVC coil electrode 38, respectively. Hence, the DC resistance may be measured between the coil electrode 36 and the contact of connector 31 which contact the electrode 36 by measuring the DC resistance between wire 152 and wire 156. Similarly, the DC resistance may be measured between the SVC coil electrode and the contact of connector 31 which is connected thereto by measuring the DC resistance between wire 154 and wire 158. Hence, in this manner, the DC resistance of the defibrillation lead may be measured to determine if there is proper continuity between the coil electrodes and their respective contacts on connector 31.

Figure 10:
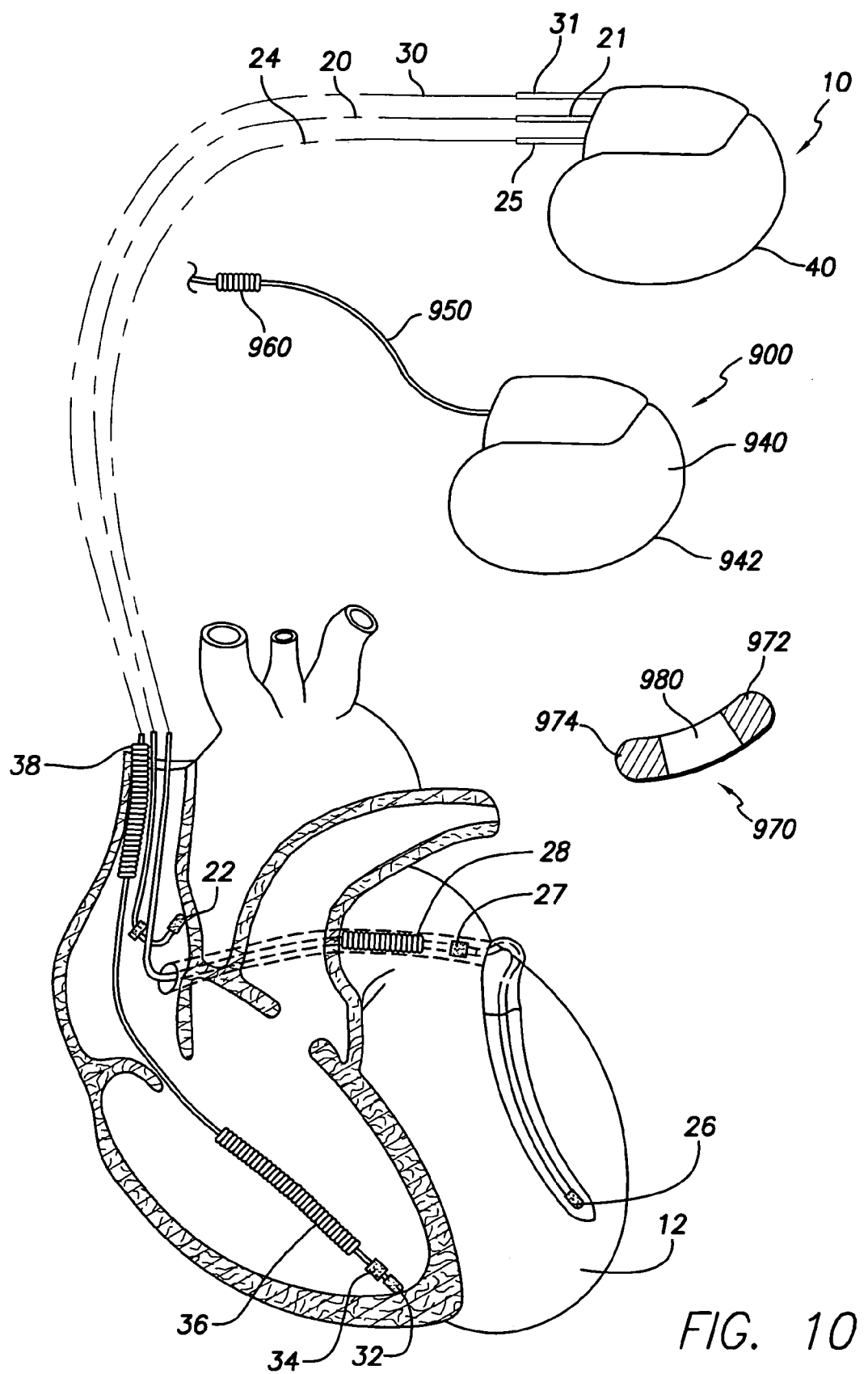
FIG. 10 is a simplified diagram illustrating subcutaneous defibrillator embodiments.

FIG. 10 shows a subcutaneous defibrillation system 900 according to a further illustrative embodiment. The subcutaneous defibrillation system differs from an implantable cardiac defibrillator in that the lead system is entirely external to the heart but still within the body. The device itself may be considered "implanted" because it is beneath the skin of the patient. However, its placement may be very different.

As will be noted in FIG. 10, the system 900 includes a defibrillator device 940. It may be positioned below the heart within the abdomen. The device 940 may be similar to the device 10 also shown in FIG. 10 and configured as previously described. However, the device 940 may, but need not, include any pacing functionality. Similarly, in this embodiment, the device 10 may, but need not, include any defibrillation functionality. To that end, the defibrillation electrodes 36, 38, and 28 may be eliminated.

The system 900 further includes at least one lead 950 having a large area defibrillation electrode 960. The electrode 960 is placed beneath the patient's skin above the heart so that a defibrillation shock may be applied between the electrode 960 and the device case 942. Subcutaneous devices such as device 940 may be desirable where a patient already has a pacing device or where a patient does not require pacing therapy.

The defibrillation output requirements (threshold) of the device 940 may be estimated without induction of fibrillation. In general, this may be achieved by applying a relatively low voltage test pulse between the device case 942 and electrode 960. An induced voltage may then be monitored by the device 10 between a pair of electrodes implanted in the heart. The voltage measured, together with the electrode spacing, enables the resulting field within the heart to be determined. The applied voltage may then be appropriately scaled to achieve the desired electrical field for defibrillation. The electrodes used to measure the field may be chronic electrodes, such as those shown in FIG. 10 associated with device 10 or they may be temporary electrodes.

As an example of the above, a test pulse of 10 volts at 10 kilohertz (kHz) may be applied between the device case 942 and electrode 920. As this voltage is applied, the induced voltage may be measured by the device 10 between the right ventricular tip electrode 82 and the right ventricular ring electrode 34. Let's assume that the voltage reading was 50 millivolts (0.050 volts). Let us also assume that there is a 5 volt electrode interface loss so that 5 volts actually produced the 0.050 volts across electrodes 32 and 34. The spacing between electrodes 32 and 34 may commonly be 1 cm. Hence, the field produced by the 5 volts is 0.050/1 cm (v/cm). Since a 4 volt/cm electric field across the heart is generally required for defibrillation, the voltage "X" needed for defibrillation between the device case 942 and the electrode 960 would be:

$$X = \frac{4\frac{v}{cm} \cdot 5v}{.05\frac{v}{cm}} = 400 \text{ volts}$$

To raise the probability of success, the result may be increased by 100 volts. Alternatively, full output of, for example, 1000 volts may be employed for assured success with the foregoing measurement being made to confirm electrode placement and device defibrillation capability.

Other measuring electrode configuration may be employed. For example, the device 10 may measure induced voltage between the right ventricular tip electrode 32 and the device case 40 or between the right ventricular tip electrode 32 and the left ventricular tip electrode 26, for example. Of course, other measuring electrode configurations are possible.

FIG. 10 also shows another subcutaneous defibrillation device 970. It includes a defibrillation device case 980 upon which are formed or carried large area defibrillation electrodes 972 and 974. The advantage of device 970 is that it does not require separate lead placement since the electrodes 972 and 974 are carried by the device case 980.

While the illustrative embodiments have been described, it is understood that numerous modifications and variations could be made thereto by those skilled in the art without departing from the spirit and scope of the invention. For example, the evaluation and conditioning for defibrillation therapy described herein may also be practiced in defibrillation assemblies for defibrillating the left side of the heart or for defibrillating the atria.

What is claimed is:

1. An implantable cardiac defibrillation assembly comprising:
at least one implantable lead including a defibrillation electrode adapted for placement in a chamber of the heart and including a connector, the lead further adapted to provide near-field and far-field pacing electrode configurations; and
an implantable defibrillation device having a ventricular pacing pulse generator that provides ventricular pacing pulses and a pulse generator that provides defibrillation pulses, the device configured to receive the connector to couple the defibrillation electrode to the pulse generator, the device further including a system that evaluates and conditions the assembly to provide defibrillation therapy to the heart without requiring arrhythmia induction of the heart, wherein the system is operative to:
generate a test pulse, measure an electric field resulting from the test pulse, and to determine a test-pulse defibrillation threshold based on the measured electric field generated by the test pulse and a predefined electric field value required to defibrillate the heart;
measure a near-field pacing threshold and determine a near-field-pacing defibrillation threshold based on the measured near-field pacing threshold and a predefined scaling factor;
measure a far-field pacing threshold and determine a far-field-pacing defibrillation threshold based on the measured far-field pacing threshold and a predefined scaling factor; and
determine a defibrillation threshold based on an average of at least two of a test-pulse defibrillation threshold, a near-field-pacing-threshold defibrillation threshold and a far-field-pacing-threshold defibrillation threshold.

2. The assembly of claim 1 wherein the at least one implantable lead has a lead DC resistance between the connector and the defibrillation electrode, and wherein the assembly further comprises a DC resistance measuring circuit that measures the lead DC resistance responsive to the device receiving the connector coupling the defibrillation electrode to the pulse generator.

3. The assembly of claim 2 further comprising a display that displays the measured lead DC resistance.

4. The assembly of claim 2 further comprising an alarm that provides a perceptible indication when the lead DC resistance is outside of a predetermined DC resistance range.

5. The assembly of claim 1 further including a ventricular sensing electrode that senses ventricular electrical activity including R waves of the heart, wherein the device includes a ventricular sensing circuit that is adapted to be coupled to the ventricular sensing electrode that senses the ventricular activity sensed by the ventricular sensing electrode, and wherein the system further comprises a confirmation circuit that confirms that the sensing ventricular electrode and ventricular sensing circuit are able to sense R waves of the heart.

6. The assembly of claim 5 wherein the confirmation circuit confirms acceptable R wave amplitude and/or slew rate.

7. The assembly of claim 5 further including an atrial sensing electrode that senses atrial activity including P waves of the heart, wherein the device includes an atrial sensing circuit that is adapted to be coupled to the atrial sensing electrode that senses the atrial activity sensed by the atrial sensing electrode, and wherein the confirmation circuit confirms sensing of an R wave corresponding to each sensed P wave.

8. The assembly of claim 7 wherein the device includes a relatively long AV delay to enable sensing of conducted R waves.

9. The assembly of claim 5 wherein the device includes a relatively long escape interval.

10. The assembly of claim 1 wherein the system is operative to set the pulse generator to a defibrillation voltage above the defibrillation threshold.

11. The assembly of claim 1 wherein the device includes a conductive enclosure, wherein the system is further operative to cause the pulse generator to apply a test pulse of a given voltage between the device enclosure and the defibrillation electrode and to measure an induced voltage induced by the test pulse and indicative of a corresponding defibrillation electrical field.

12. An implantable cardiac defibrillation assembly comprising:
implantable lead means including a defibrillation electrode for making electrical contact with a chamber of the heart and including a connector; and device means having pulse generating means for providing defibrillation pulses and ventricular pacing pulse generating means for providing near-field and far-field ventricular pacing pulses and being configured for receiving the connector for coupling the defibrillation electrode to the pulse generating means, the device means further comprising:

means for generating a test pulse, means for measuring an electric field resulting from the test pulse, and means for determining a defibrillation threshold based on the measured electric field generated by the test pulse and a predefined electric field value required to defibrillate the heart;

means for measuring a near-field pacing threshold and determining a near-field-pacing defibrillation threshold based on the measured near-field pacing threshold and a predefined scaling factor;

means for measuring a far-field pacing threshold and determining a far-field-pacing defibrillation threshold based on one of the measured far-field pacing threshold and a predefined scaling factor; and means for determining a defibrillation threshold based on an average of at least two of a test-pulse defibrillation threshold, a near-field-pacing-threshold defibrillation threshold and a far-field-pacing-threshold defibrillation threshold.

13. In a procedure of implanting a cardiac defibrillation assembly, a method comprising:

providing at least one implantable lead including a defibrillation electrode adapted for placement in a chamber of the heart and including a connector;

providing an implantable defibrillation device having a pulse generator that provides defibrillation pulses and that is configured to receive the connector to couple the defibrillation electrode to the pulse generator; and determining at least two of a test-pulse defibrillation threshold, a near-field-pacing-threshold defibrillation threshold and a far-field-pacing-threshold defibrillation threshold and thereafter computing a defibrillation threshold average from the at least two measurements, wherein determining a test-pulse defibrillation threshold comprises generating a test pulse, measuring an electric field resulting from the test pulse, and determining the test-pulse defibrillation threshold based on the measured electric field generated by the test pulse and a predefined electric field value required to defibrillate the heart; determining a near-field-pacing-threshold defibrillation comprises providing a ventricular near-field pulse, measuring a near-field pacing threshold, and determining a near-field-pacing-threshold defibrillation threshold based on the measured near-field pacing threshold and a predefined scaling factor; and determining a far-field-pacing-threshold defibrillation comprises providing a ventricular far-field pulse, measuring a far-field pacing threshold, and determining a far-field-pacing-threshold defibrillation threshold based on the measured far-field pacing threshold and a predefined scaling factor.

* * * * *